(12) United States Patent
Jacob

(10) Patent No.: US 6,218,367 B1
(45) Date of Patent: Apr. 17, 2001

(54) PACLITAXEL-CARBOHYDRATE CONJUGATES: DESIGN, SYNTHESIS AND BIOLOGICAL EVALUATIONS

(75) Inventor: James N Jacob, Saunderstown, RI (US)

(73) Assignee: Organomed Corporation, North Kingtown, RI (US)

( * ) Notice: Subject to any disclaimer, the term of this patent is extended or adjusted under 35 U.S.C. 154(b) by 0 days.

(21) Appl. No.: 09/395,843

(22) Filed: Sep. 14, 1999

Related U.S. Application Data
(60) Provisional application No. 60/100,419, filed on Sep. 15, 1998.

(51) Int. Cl.[7] ................................................. H61K 31/70
(52) U.S. Cl. ............................ 514/25; 536/17.9; 536/18.1
(58) Field of Search .................... 514/25, 449; 536/18.1, 536/17.9; 549/448

(56) References Cited

U.S. PATENT DOCUMENTS

| | | | |
|---|---|---|---|
| 5,489,589 | 2/1996 | Whittman et al. | 514/232.8 |
| 5,677,286 | * 10/1997 | Srull et al. | 514/25 |
| 5,801,191 | 9/1998 | Bressi et al. | 514/449 |

OTHER PUBLICATIONS

Bissery, M.–C. et al. "Experimental antitumor activity of taxotere (RP 56976, NSC 628503), a taxol analogue", Cancer Res. 51: 4845–4852 (1991).

Boyd, M. R. et al. "Some practical considerations and applications of the national cancer institute in vitro anticancer drug discovery screen", Drug Dev. Res. 34: 91–109 (1995).

Deutsch, H. M. et al. "Synthesis fo congeners and prodrugs. 3. Water–soluble prodrugs of taxol with potent antitumor activity", J. Med. Chem. 32: 788–792 (1989).

Greenwald, R. B. et al. "Drug delivery systems: water soluble taxol 2'–poly(ethylene glycol) ester prodrugs—design and in vitro effectiveness", J. Med. Chem. 39: 424–431 (1996).

Li, C. et al. "Complete regression of well–established tumors using a novel water–soluble poly(L–glutamic acid)–paclitaxel conjugate", Cancer Res. 58: 2404–2409 (1998).

Mathew, A. W. et al. "Synthesis and evalutation of some water–soluble prodrugs and derivatives of taxol with antitumor activity", J. Med. Chem. 35: 145–151 (1991).

Monks, A. et al. "Feasibility of a high–flux anticancer drug screen using a diverse panel of cultured human tumor cell lines", J. Natl. Cancer Inst. 83: 757–766 (1991).

Nicolauo, K. C. et al. "A water–soluble prodrug of taxol with self–assembling properties", Angew. Chem. Int., Ed. 33: 1583–1587 (1994).

Paloma, L. G. et al. "Conformation of a water–soluble derivative of taxol in water by 2D–NMR spectroscopy", Curr. Biol. 1: 107–112 (1994).

Rose, W. C. et al. "Preclinical antitumor activity of water–soluble paclitaxel derivatives", Cancer Chemother. Pharmacol. 39: 486–492 (1997).

Souto, A. A. et al. "New flourescent water soluble taxol derivatives", Angew. Chem. Int. Engl. 34: 2710–2712 (1995).

Vyas, D. M. et al. "Synthesis and antitumor evaluation of water soluble taxol phosphates", Bio–organic and Medicinal Chem. Letters, 3: 1357–1360 (1993).

* cited by examiner

*Primary Examiner*—Elli Peselev
(74) *Attorney, Agent, or Firm*—Peter F. Corless; Christine C. O'Day; Edwards & Angell, LLP

(57) ABSTRACT

The present invention provides novel, water soluble, carbohydrate derivatives of paclitaxel, methods of treatment and pharmaceutical compositions that utilize or comprise one or more of such compounds. The compounds of the invention are modified at the 2' or 7 position of paclitaxel and have the general formula [paclitaxel]-[link]$_{1-2}$-[sugar]. These compounds show improved biological activity toward many cancer cell lines as compared to paclitaxel. Additionally, the conjugates are made from natural non-toxic materials which, when released, will be adsorbed as part of the body components.

36 Claims, 8 Drawing Sheets

MEAN GRAPHS FOR CHACKOL AND PACLITAXEL

CHACKOL

| Panel/Cell Line | Log₁₄TGI | TGI |
|---|---|---|
| Leukemia | | |
| CCRF-CEM | | |
| HL/60(TB) | | |
| MOLT-4 | > -6.00 | |
| RPMI-8226 | -9.10 | |
| SR | > -6.00 | |
| Non-Small Cell Lung Cancer | | |
| A549/ATCC | > -6.00 | |
| EKVX | > -6.00 | |
| HOP-82 | > -6.00 | |
| HOP-92 | > -6.00 | |
| NCI-H226 | > -6.00 | |
| NCI-H23 | > -6.00 | |
| NCI-H332M | > -6.00 | |
| NCI-H522 | -9.24 | |
| Colon Cancer | | |
| COLO 205 | -8.89 | |
| HCC-2998 | -9.34 | |
| HCT-116 | > -6.00 | |
| HCT-15 | > -6.00 | |
| HT29 | -9.38 | |
| KM12 | | |
| SW-620 | | |
| CNS Cancer | | |
| SF-268 | > -6.00 | |
| SF-295 | -8.05 | |
| SF-539 | -9.22 | |
| SNB-19 | > -6.00 | |
| SNB-75 | -9.07 | |
| U251 | | |

PACLITAXEL-CARBOHYDRATE CONJUGATES: DESIGN, SYNTHESIS AND BIOLOGICAL EVALUATIONS

This application claims the benefit of U.S. Provisional Application Number 60/100,419, filed Sept. 15, 1998, which is incorporated herein by reference.

BACKGROUND OF THE INVENTION

1. Field of the Invention

The present invention relates to novel anti-tumor compounds, methods of treatment and pharmaceutical compositions that utilize or comprise one or more such compounds. Compounds of the invention are novel carbohydrate derivatives of paclitaxel that are more water soluble and have better biological properties compared to paclitaxel.

2. Background

Paclitaxel (Taxol®) is a chemotherapeutic agent that was originally isolated from the bark of the Pacific yew, *Taxus brevifolia*. It has been shown to have antitumor activity toward a wide variety of cancers including breast, ovarian, melanoma, lung, colon, leukemias and others. Paclitaxel acts by promoting tubulin assembly and by stabilizing the microtubules to prevent their disassociation into free tubulin. Actively dividing cells are thus particularly sensitive to paclitaxel and become arrested at the G2/mitosis cell cycle transition.

Although paclitaxel has promising antitumor activity, it has been difficult to develop for clinical treatments due to its very low solubility in water. Paclitaxel is administered in large volume, low concentration formulations with Cremophor EL which results in many patients developing side effects such as hypersensitivity reactions. Thus, it would be extremely desirable to develop novel paclitaxel derivatives that have increased water solubility while maintaining or surpassing the cytotoxic activity of paclitaxel itself.

See also: Wittman et al., U.S. Pat. No. 5,942,184; Bressi et al., U.S. Pat. No. 5,801,191; Vyas, D. M. et al., "Synthesis and Anti-tumor Evaluation of Water Soluble Taxol Phosphates", Bio-organic and Medicinal Chemistry Letters, 3, 1357–1360, 1993; Greenwald, R. W. et al., "Drug Delivery Systems: Water soluble Taxol 2'-Poly(ethylene glycol) Ester Pro-drugs-Design and in vitro Effectiveness", J. Med. Chem. 39, 424–431, 1996; Mathew, A. E. et al., "Synthesis and Evaluation of Some Water Soluble Prodrugs and Derivatives of Taxol with Anti-tumor Activity", J. Med. Chem., 35, 145–151, 1992; Nicolaou, K. C. et al., "A Water-soluble Prodrug of Taxol with Self-assembling Properties", Angew. Chem. Int., Ed., 33, 1583–1587, 1994; Souto, A. A. et al., "New Fluorescent Water Soluble Taxol Derivatives", Angew. Chem. Int., Engl. 34, 2710–2712, 1995; Bissery, M. C. et al., "Experimental Anti-tumor Activity of Taxotere (RP 56976, NSC 628503), a Taxol Analogue", Cancer Res., 51, 4845–4852, 1991; Deutsch, H. M. et al., "Synthesis of Congeners and Pro-drugs of Taxol with Potent Anti-tumor Activity", J. Med. Chem., 32, 788–792, 1989.

SUMMARY OF THE INVENTION

The present invention provides novel carbohydrate derivatives of paclitaxel, and methods of treatment and pharmaceutical compositions that utilize or comprise one or more of such compounds. Preferred compounds are more water soluble and have better biological properties compared to paclitaxel. Moreover, preferred compounds of the invention are made from natural non-toxic materials which, when released, will be adsorbed as part of the body components.

The invention thus provides methods for treating an animal bearing susceptible primary or secondary tumors including tumors in the breast, prostate, ovary, central nervous system, brain, colon, lung, skin, etc. or disseminated tumors such as leukemic cells etc. The invention also provides methods which comprise using one or more carbohydrate conjugated paclitaxel derivative to treat susceptible tumors in a mammal, especially a human. The invention further provides pharmaceutical composites that comprise one or more compounds of the invention and a suitable carrier.

The present invention provides compounds having the following general formula:

[paclitaxel]-[link]$_{1-2}$-[sugar].

The link group(s) attached to the paclitaxel and sugar moieties are comprised of dicarboxylic acids, HOOC(CH$_2$)$_n$COOH, with from 2 to 12 carbon atoms, preferably with from 2 to 6 carbon atoms and most preferably with four carbon atoms. The link group(s) may also comprise amino acids and amino dicarboxylic acids preferably with from 1 to 12 carbon atoms and more preferably with from 1 to 6 carbon atoms. Non-limiting examples include succinic acid, glutamic acid and γ-aminobutyric acid. The link group is attached to the 2' or 7 hydroxyl group of paclitaxel via an ester conjugation.

The sugar moiety is comprised of mono-, di-, oligo- or poly-saccharides wherein each monosaccharide unit comprises from 3 to 8 carbons, preferably from 3 to 6 carbons, containing polyhydroxy groups or polyhydroxy and amino groups. Non-limiting examples include glycerol, ribose, fructose, glucose, glucosamine, mannose, galactose, maltose, cellobiose, sucrose, starch, amylose, amylopectin, glycogen and cellulose. The hydroxyl and amino groups are present as free or protected groups containing e.g. hydrogens and/or halogens. Preferred protecting groups include acetonide, t-butoxy carbonyl groups, etc. The sugar moiety is preferably conjugated as an ester or an amide.

Each monosaccharide unit of the sugar moiety may be of the L or D configuration and a cyclic monosaccharide unit may contain a 5 or 6 membered ring of the α or β conformation. Disaccharides may be comprised of two identical or two dissimilar monosaccharide units. Oligosaccharides may be comprised of from 2 to 10 monosaccharides and may be homopolymers, heteropolymers or cyclic polysugars. Polysaccharides may be homoglycans or heteroglycans and may be branched or unbranched polymeric chains. The di-, oligo- and poly-saccharides may be comprised of 1→4, 1→6 or a mixture of 1→4 and 1→6 linkages. The sugar moiety may be attached to the link group through any of the hydroxyl or amino groups of the carbohydrate.

More specifically, the invention provides compounds of the following formula (Formula I) that are useful as anti-tumor treatments:

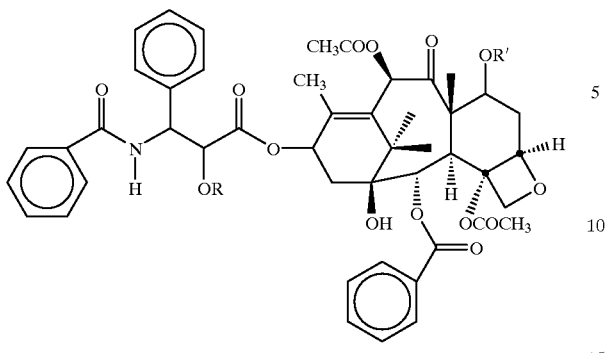

wherein R and R' each individually consist of a hydrogen atom or a group containing a sugar molecule, glucose or glucosamine.

The R and R' substituents are both adjacent to chiral carbons as shown in the above structure (Formula I). Thus, the compound contains two chiral centers and can form 4 diastereomers. The invention includes both racemic mixtures and optically enriched mixtures of Formula I. An optically enriched mixture contains substantially more (e.g., about 60 mole %, 70 mole %, 80 mole %, 90 mole %, 95 mole %, 98 mole % or more) of one enantiomer of Formula I than the other stereoisomers. For use in the therapeutic methods of the invention, preferably a substantially pure optically active mixture is employed, e.g. a mixture containing at least about 92 mole % or 99 mole % or more of one enantiomer of Formula I. Optically enriched mixtures can be obtained by known procedures, e.g., column chromatography using an optically active binding material or by use of optically active reagents or enantiomerically selective reactions.

DETAILED DESCRIPTION OF THE INVENTION

Figure 1A:
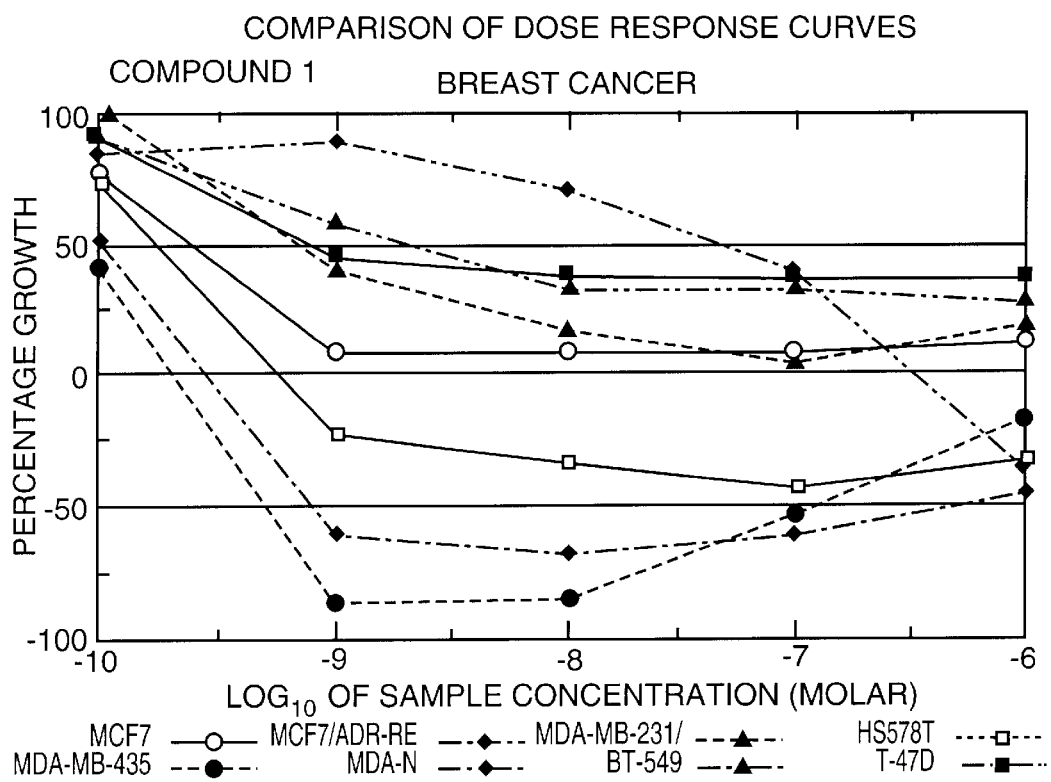
FIG. 1 provides a graph showing the dose response curves for compound 1 (chackol) (1a) and paclitaxel (1b) for breast cancer. The graphs for chackol extend one log unit lower than those for paclitaxel showing the greater activity of chackol.
Figure 1B:
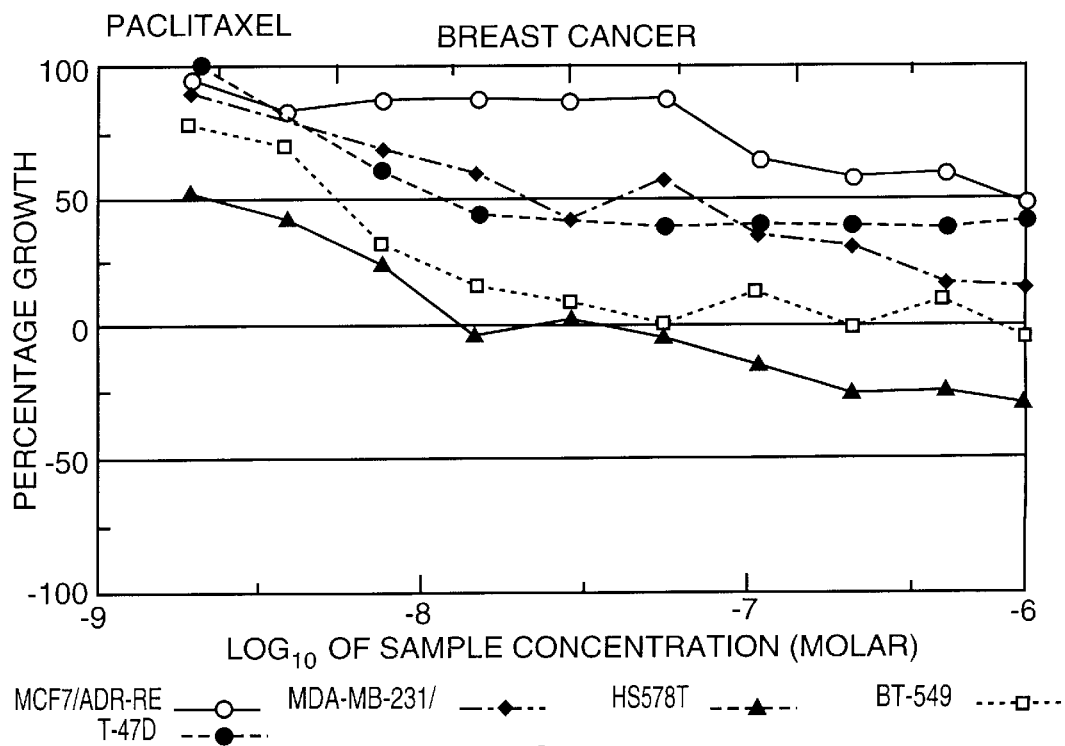
Figure 2A:
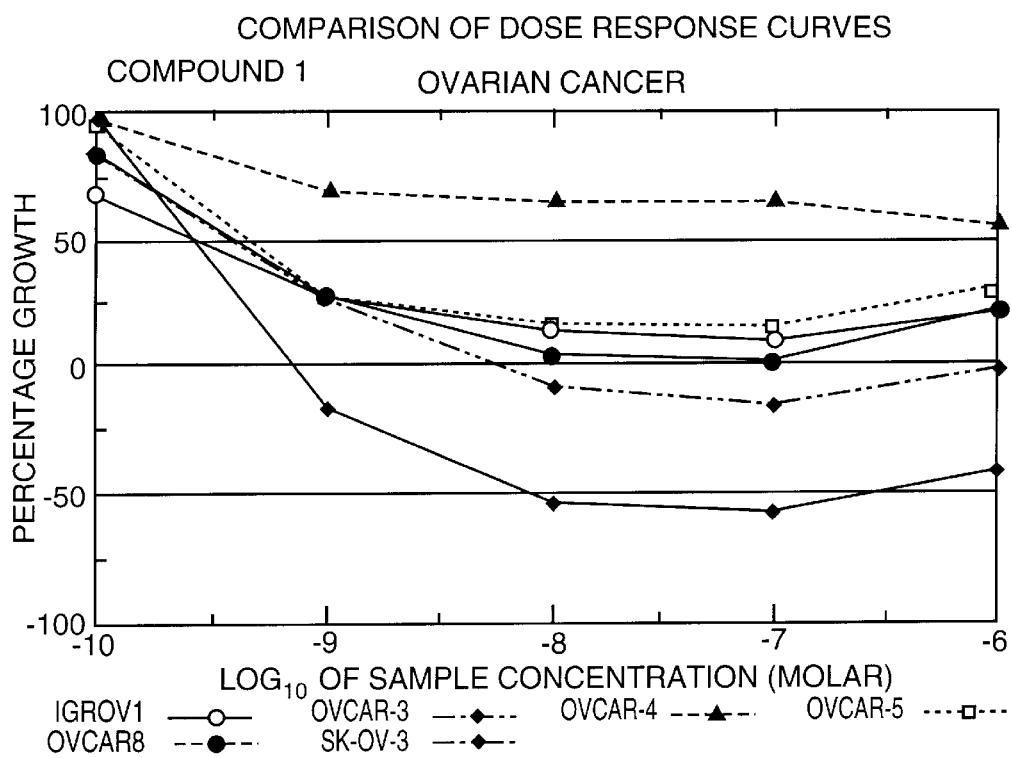
FIG. 2 provides a graph showing the dose response curves for compound 1 (chackol) (2a) and paclitaxel (2b) for ovarian cancer. The graphs for chackol extend one log unit lower than those for paclitaxel showing the greater activity of chackol.
Figure 2B:
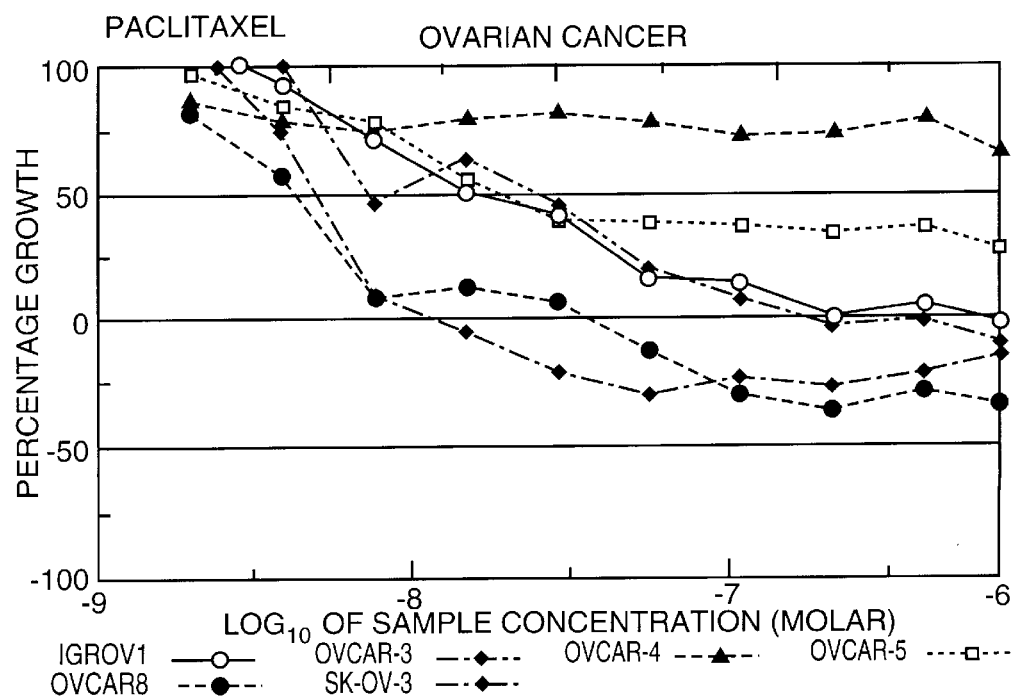
Figure 3A:
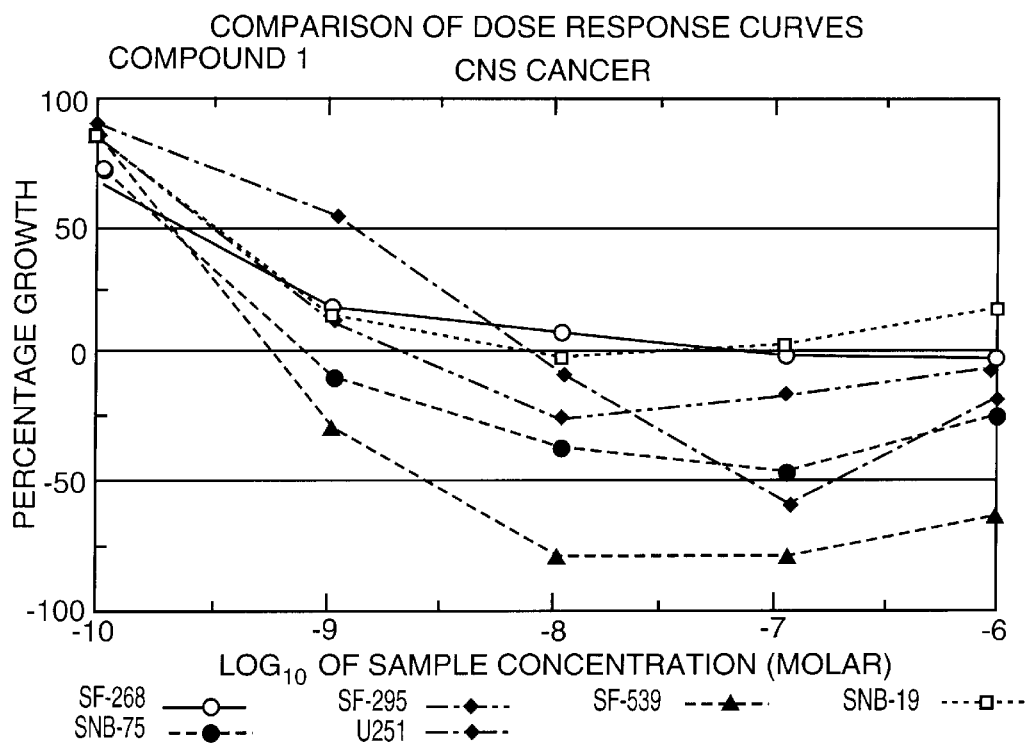
FIG. 3 provides a graph showing the dose response curves for compound 1 (chackol) (3a) and paclitaxel (3b) for CNS cancer. The graphs for chackol extend one log unit lower than those for paclitaxel showing the greater activity of chackol.
Figure 3B:
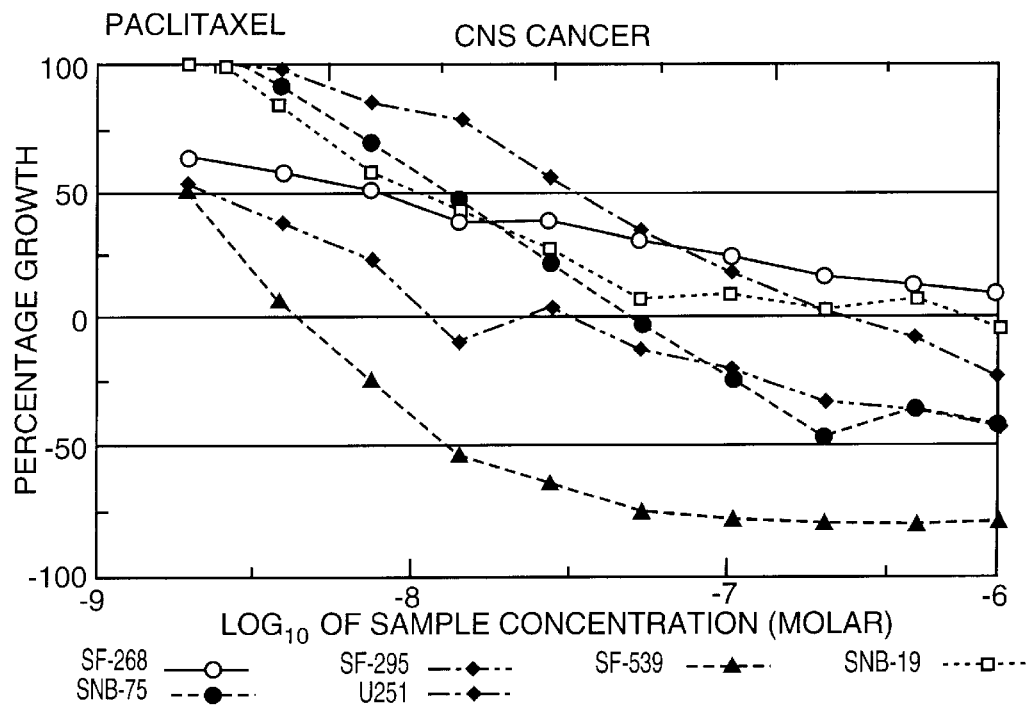
Figure 4A:
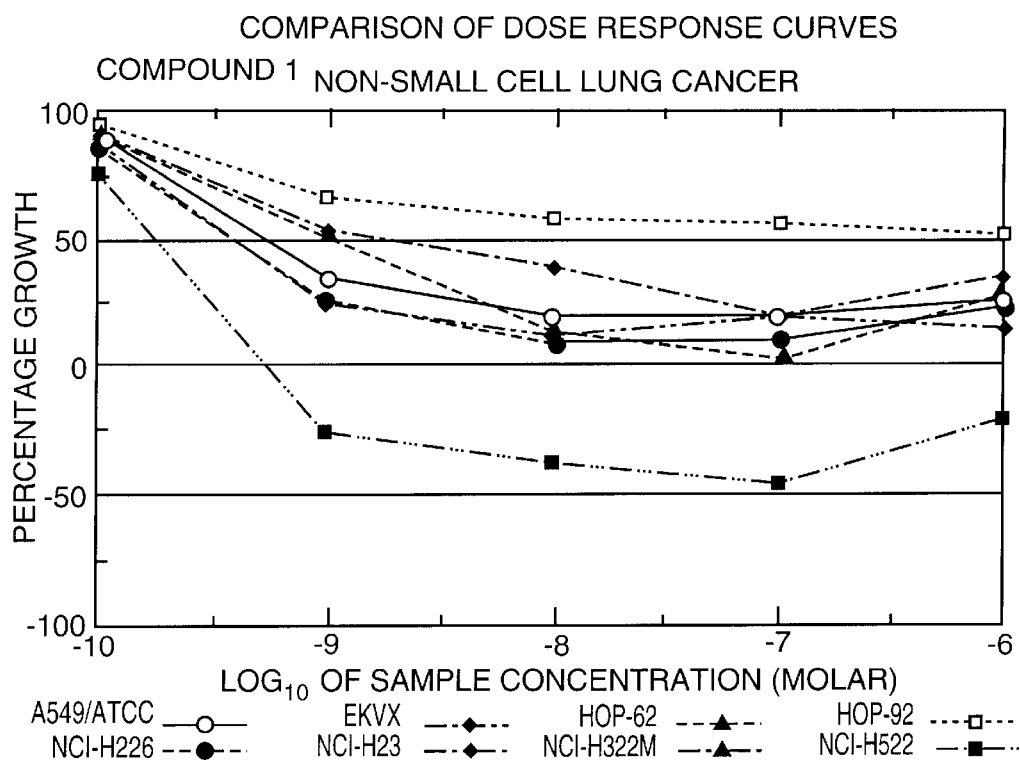
FIG. 4 provides a graph showing the dose response curves for compound 1 (chackol) (4a) and paclitaxel (4b) for non-small cell lung cancer. The graphs for chackol extend one log unit lower than those for paclitaxel showing the greater activity of chackol.
Figure 4B:
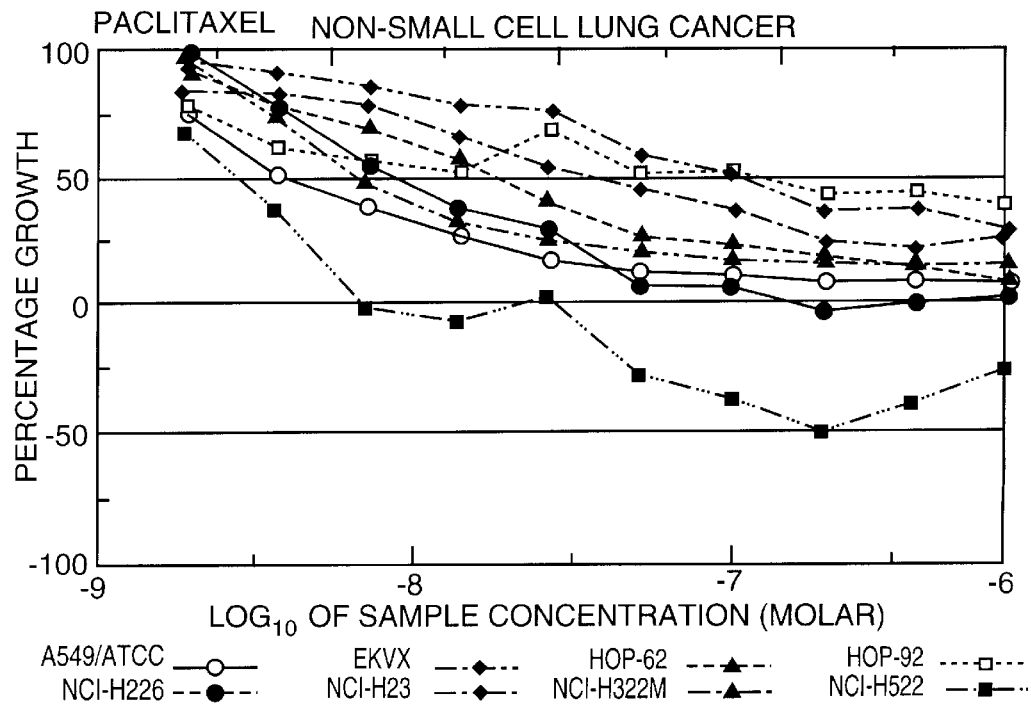

We have now discovered that compounds having the following Formula I are useful as anti-tumor drugs for the treatment of mammals, particularly humans, that have primary, secondary or disseminated tumors:

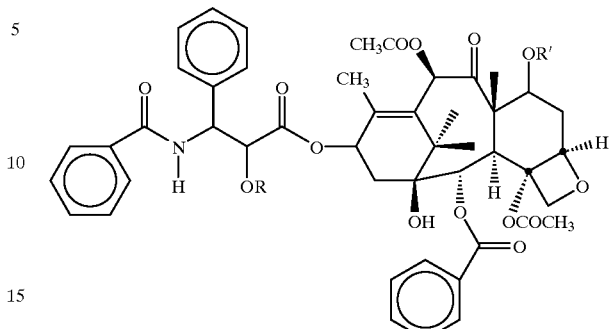

wherein R and R' are selected from a group consisting of a hydrogen atom or a group containing a sugar molecule. Each monosaccharide unit of the sugar molecule may be comprised of mono-, di-, oligo- or polysaccharides wherein each monosaccharide unit comprises from 3 to 8 carbons, preferably from 3 to 6 carbons, containing polyhydroxy groups or polyhydroxy and amino groups. Non-limiting examples include glycerol, ribose, fructose, glucose, glucosamine, mannose, galactose, maltose, cellobiose, sucrose, starch, amylose, amylopectin, glycogen and cellulose. The hydroxyl and amino groups are present as free or protected groups containing e.g. hydrogens and/or halogens. Preferred protecting groups include acetonide, t-butoxy carbonyl groups, etc. The monosaccharide unit may be of the L or D configuration and a cyclic monosaccharide unit may contain a 5 or 6 membered ring of the α or β conformation. Disaccharides may be comprised of two identical or two dissimilar monosaccharide units. Oligosaccharides may be comprised of from 2 to 10 monosaccharides and may be homopolymers, heteropolymers or cyclic polysugars. Polysaccharides may be homoglycans or heteroglycans and may be branched or unbranched polymeric chains. The di-, oligo- and poly-saccharides may be comprised of 1→4, 1→6 or a mixture of 1→4 and 1→6 linkages. The sugar moiety may be attached to the link group through any of the hydroxyl or amino groups of the carbohydrate.

Preferred compounds of the invention comprise R or R' groups containing glucose or glucosamine.

Particularly preferred compounds of the invention are 2'-(GABA-succinoyl)paclitaxel, 2'-(glucose-GABA-succinoyl)paclitaxel, 2'-(glucose-succinoyl)paclitaxel, 2'-(glucose-glutamyl)paclitaxel, 2'-(glucosamide-GABA-succinoyl)paclitaxel, 2'-(glucoseamide-succinoyl)paclitaxel, 2'-(glucoseamide-glutamyl)paclitaxel, 7-(GABA-succinoyl) paclitaxel, 7-(glucose-GABA-succinoyl)paclitaxel, 7-(glucose-succinoyl)paclitaxel, 7-(glucose-glutamyl) paclitaxel, 7-(glucosamide-GABA-succinoyl)paclitaxel, 7-(glucoseamide-succinoyl)paclitaxel and 7-(glucoseamide-glutamyl)paclitaxel.

Compounds of the invention can be prepared as generally depicted in the following schemes I to III.

SCHEME I

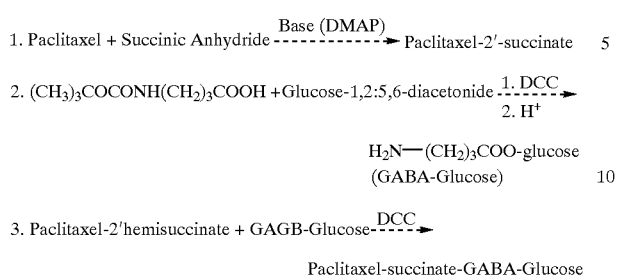

3. Paclitaxel-2'hemisuccinate + GAGB-Glucose $\xrightarrow{DCC}$

Paclitaxel-succinate-GABA-Glucose

DCC: Dicyclohexlycabodiimide
DMAP: Dimethylaminopyridine

Structure of [Paclitaxel]-[succinate]-[GABA]-[glucose]:

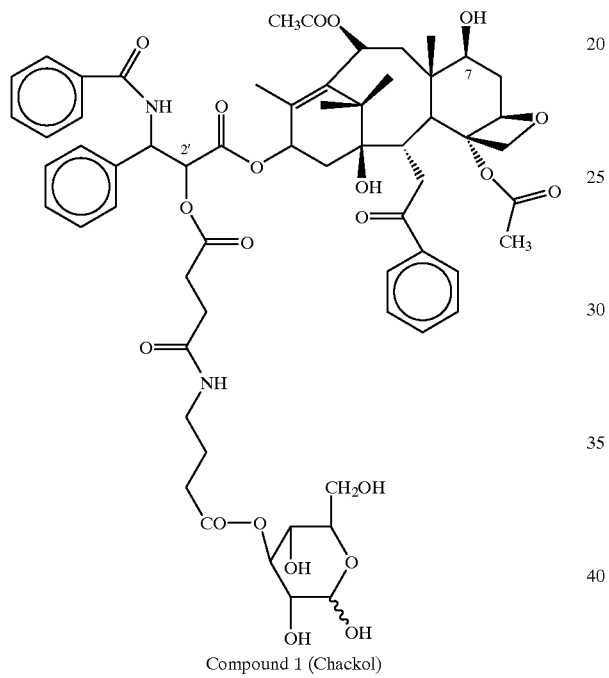

Compound 1 (Chackol)

Scheme I shows the preparation of [Paclitaxel]-[succinate]-[GABA]-[glucose]. Paclitaxel is converted to its 2'-hemisuccinate by treating with succinic anhydride and a suitable base. This hemisuccinate is condensed with the amino group of glucose-GABA ester. The glucose-GABA ester was prepared from N-Boc-γ-aminobutyric acid and glucose-1,2:5,6-diacetonide followed by deprotection of the Boc and acetonide groups.

SCHEME II

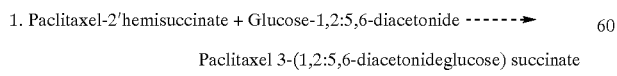

Paclitaxel 3-(1,2:5,6-diacetonideglucose) succinate

Structure of [paclitaxel]-[succinate]-glucose-1,2:5,6-diacetonide:

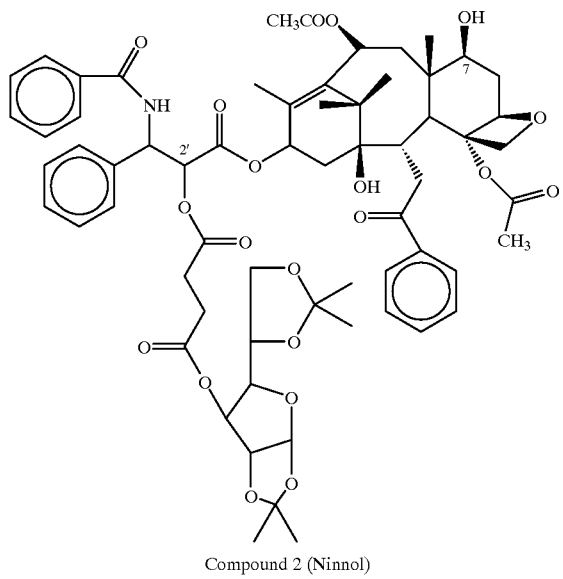

Compound 2 (Ninnol)

Scheme II shows the preparation of [Paclitaxel]-[succinate]-glucose-1,2:5,6-diacetonide. Paclitaxel is converted to paclitaxel-2'-hemisuccinate and this hemisuccinate was condensed with glucose-1,2:5,6-diacetonide using DCC.

SCHEME III

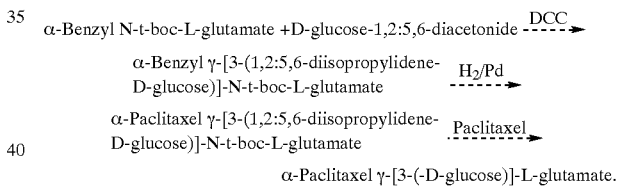

α-Paclitaxel γ-[3-(-D-glucose)]-L-glutamate.

Structure of [Paclitaxel]-[Glutamate]-[Glucose]:

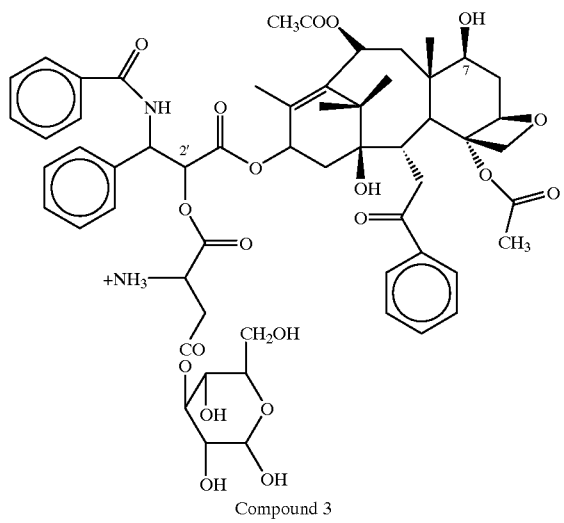

Compound 3

Scheme III shows the preparation of [Paclitaxel]-[Glutamate]-[Glucose]. α-Benzyl-N-t-boc-L-glutamate was condensed with diacetone-D-glucose. The product, α-benzyl γ-3-(1,2:5,6-diisopropyldene-D-glucose)-N-t-boc-L-glutamate was hydrogenolysed to get γ-[3-(1,2:5,6-diisopropylidene-D-glucose)]-N-t-boc-L-glutamate. This compound was condensed with paclitaxel to get α-paclitaxel γ-[3-(1,2:5,6-diisopropylidene-D-glucose)]-N-t-boc-L-glutamate. This compound was treated with acid to remove the boc and the acetonide protecting groups.

Compounds of the invention will be useful in treating mammals, particularly humans, bearing susceptible primary, secondary or disseminated tumors. Specific examples of tumors which may be treated in accordance with the invention include breast, prostate, ovary, central nervous system, brain, lung, skin, colon and leukemic cells. The invention also provides methods for administering one or more compounds of formula I to treat tumors in a mammal. Compounds of the invention may also be used therapeutically in conjunction with other anti-cancer treatments.

Administration of compounds of the invention may be made by a variety of suitable routes including oral, topical (including transdermal, buccal or sublingal), nasal and parenteral (including intraperitoneal, subcutaneous, intravenous, intradermal or intramuscular injection) or other suitable forms. It will be appreciated that the actual preferred amounts of active compounds in a given therapy will vary according to the specific compound being utilized, the particular compositions formulated, the mode of application, the particular site of administration, the condition and age of the recipient, etc. Optimal administration rates for a given protocol of administration can be readily ascertained by those skilled in the art using conventional dosage determination tests. Dosages may be generally in the range of 0.5 mg to 10 mg/kg body weight.

While one or more of the compounds of the invention may be administered alone, they also may be present as part of a pharmaceutical composition in mixture with a pharmaceutically acceptable organic or inorganic carrier substance suitable for parenteral, oral or other desired route of administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, glucose, mannose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, cyclodextrans, fish oils, components of fish oils, triglycerides, ω-3-fatty acids, ω-3-fatty acid esters, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds. These compositions can also be freeze-dried and reconstituted in appropriate solvents.

For parenteral application, particularly suitable are solutions, preferably oily or aqueous solutions as well as suspensions, emulsions or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differently degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23:238–252 (1965); F. Olson et al., *Biochim. Biophys. Acta*, 557:9–23 (1979); F. Szoka et al., *Proc. Nat. Acad. Sci.*, 75:4194–4198 (1978); S. Kim et al., *Biochim. Biophys. Acta*, 728:339–348 (1983); and Mayer et al., *Biochim. Biophys. Acta*, 858:161–168 (1986).

The liposome may be made from any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids may also be used e.g., dimyristoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis (oleoyloxy)-3-(trimethyl ammonio)propane (DOTAP), N-[1-(2,3-dioleoyl)propyl]-N,N,N-trimethylammonium choloride (DOTMA), and other cationic lipids may be incorporated into the liposomes. The relative amounts of one or more compounds of Formula I and additives used in the liposomes may vary relatively widely. Liposomes of the invention suitably contain about 60 to 90 mole percent of natural or synthetic phospholipid; cholesterol, cholesterol hemisuccinate, fatty acids or cationic lipids may be used in amounts ranging from 0 to 50 mole percent; and the one or more therapeutic compounds of the invention may be suitably present in amounts of from about 0.01 to about 50 mole percent.

All documents mentioned herein are incorporated herein by reference.

The present invention is further illustrated by the following examples. These examples are provided to aid in the understanding of the invention and are not to be construed as limitations thereof.

In the following examples 1–5, elemental analysis were preformed by Midwest Microlabs (Indianapolis, Ind.). $^1$H NMR spectra were obtained on a Brucker 300 MHz spectrometer. Chemical shifts are in parts per million with respect to TMS. Thin layer chromatography was done on precoated (0.2 mm) silica gel 60 F-254 plates manufactured by EM Science. HPLC was performed with a Waters model pump, 7125 injector, and UV detector.

EXAMPLE 1

Preparation of (3-Glucose) GABA Paclitaxel Succinate.

Preparation of paclitaxel hemisuccinate: a mixture of paclitaxel (50 mg) was taken with 12 mg of succinic anhydride 0.70 mg of 4-dimethylamino-pyridine (DMAP) and 1.2 mL of pyridine, stirred at room temperature for 3.5 hours, concentrated and was used for further reaction without purification.

Preparation of boc-GABA-glucosediacetonide: Boc GABA (1.0 g) was mixed with diacetone D-glucose (1.28 g), DCC (1.52 g) and DMAP (88 mg) in 35 mL methylene choloride. The mixture was stirred overnight. After filtration the methylene chloride solution was washed with 10% $NaHCO_3$ solution and then 10% HCl solution, dried over $Na_2SO_4$. The crude product was purified by silica gel column chromatography, eluting with ethyl acetate, hexane (1:3). Yield was quantitative. $^1H$ NMR ($CDCL_3$): δ 1.26–1.52 (m, 21 H, —$CH_3$), 1.85 (m, 2H, —$CH_2$—), 2.40 (m, 4H, —$CH_2O$—), 3.16–3.19 (m, 2H, —$CH_2N$<), 4.01–4.25 (m, 4H, —$CH_2O$—, >CHO), 4.96 (s, 1H, —NH—), 5.23–5.24 (d, 1H, >CH—OCO—), 5.88–5.89 (d, 1H, —OCH—O). Analysis, $C_{21}H_{35}NO_9 \cdot 0.5H_2O$: Calcd., C 55.49, H 7.98, N 3.08; Found C 55.71, H 7.93, N 3.15.

Hydrolysis of Boc and acetonide groups: Boc-GABA-Glucosediacetonide (40 mg) was taken up in 5 mL methylene chloride and 0.5 mL trifluoroacetic acid and was stirred for 1 hour in an ice bath and then stirred for 20 hours at room temperature. The mixture was concentrated and used for the next step without further purification.

Synthesis of (3-glucose) GABA paclitaxel succinate: Paclitaxel hemisuccinate (55.8 mg, 0.05855 mmol), GABA glucose (0.06616 mmol) and dicyclohexylcarobdiimide (18 mg in 1 mL of pyridine) was stirred for 24 hours at room temperature. After removal of the pyridine, the crude product was purified by HPLC using a cyano column to yield 42 mg of the pure product, crystallized from ethanol, m.p. 231–232° C. Analysis, $C_{61}H_{72}N_2O_3 \cdot 4H_2O$: Calcd., C 57.53, H 6.34, N 2.20; Found, C 57.81, H 6.12, N 2.87.

EXAMPLE 2

Preparation of Paclitaxel-2'glucose-1,2:5,6-diacetone-3-succinate diester.

Paclitaxel (75 mg, 0.088 mmol), glucose-1,2:5,6-diacetone-3-succinate (33 mg, 0.092 mmol), 4-dimethylamino-pyridine (2 mg) and dicyclohexylcarbodiimide (28 mg) were dissolved in 20 mL of methylene chloride. This mixture was stirred at room temperature for 24 hours. After removal of $CH_2Cl_2$, the residue was dissolved in ethanol and purified by HPLC over a cyano column (20×300 mm) and eluted with ethanol/water (1:1), flow rate of 3.5 mL/min. After removal of the solvent, a white solid was obtained. $^1H$ NMR ($CDCl_3$—$CD_3OD$): d 1.17–2.81 (m, 38 H, —$CH_3$, —$CH_2$—), 3.81–6.39 (m, 21 H, <CH—, —$OCH_2$—. >CHOH, >CHO—, >CHNH—), 7.34–8.15 (m, 15H, ArH). Analysis: $C_{63}H_{73}NO_{22} \cdot 3H_2O$: Calcd., C 60.52, H 6.37, N 1.12; Found C 60.80, H 6.05, N 1.17.

EXAMPLE 3

Preparation of α-Paclitaxel γ-(3-glucose)glutamate.

Preparation of [α-benzyl γ-diacetone-D-glucose]-N-tBoc-L-glutamate: A mixture of α-benzyl N-t-Boc-L-glutamate (337 mg), dicyclohexylcarbodiimide (206 mg), 4-dimethylaminopyridine (80 mg), diacetone-D-glucose (260 mg) in 25 mL of methylene chloride, was stirred overnight. The mixture was filtered, concentrated and the residue was taken up in ethylacetate, washed with diluted HCl, diluted $Na_2CO_3$ and brine, dried and concentrated to get 0.50 g of the product. Purity was checked by TLC (single spot).

Preparation of α-diacetone-D-glucose-N-t-Boc-L-glutamate: A mixture of γ-diacetone-D-glucose-N-t-Boc-L-glutamate diester (0.45 g), palladium on carbon (Pd/C, 0.1 g) and methanol (50 mL) was shaken in a Parr apparatus for 9 hours. The mixture was filtered. The mixture was taken up in methylene chloride, extracted with a $K_2CO_3$ solution. The extract was acidified and extracted with $CH_2Cl_2$, washed with brine, dried and concentrated to get 90 mg of a white solid.

Preparation of α-paclitaxel γ-[3-(1,2:5,6-diisopropyldene)-L-glutamate: A mixture of γ-diacetoneglucoseglutamate (60 mg), paclitaxel (40 mg), dicyclohexylcarbodiimide (16 mg), 4-dimethylaminopyridine (7.7 mg) in 10 mL of methylene chloride was stirred overnight. The mixture was washed with diluted HCl, diluted $Na_2CO_3$ and brine, dried ($Na_2SO_4$), concentrated and the residue was taken up in 3 mL ethyl acetate and filtered and concentrated to get 74 mg. The mixture was purified on a silica gel column, eluted with ethyl acetate/hexane to get 50 mg of TLC pure product.

EXAMPLE 4

Determination of the Biological Activity of Compound 1([paclitaxel]-[succinate]-[GABA]-[glucose] or chackol) and Compound 2 ([paclitaxel]-[succinate]-glucose-1,2:5,6-diacetonide or ninnol) as Compared to Paclitaxel.

Compounds were tested as described (Monks, A. et al., (1991). J. Nat. Cancer Int., 83, 757–766; Boyd, M. R., and Paull, K. D., (1995) "Some practical considerations and applications of the National Cancer Institute In Vitro Anticancer Drug Discovery Program", Drug Development Res., 34, 91–109 in the NCI in vitro human tumor cell line screen). The compounds were examined in 60 different cell lines. The following definitions are based on the National Cancer Institute in vitro screen protocol (Boyd, M. R., and Paull, K. D., (1995) "Some practical considerations and applications of the National Cancer Institute In Vitro Anticancer Drug Discovery Screen", ibid., 34, 91–109).

The "50% growth inhibition" parameter ($GI_{50}$) is the concentration of test drug where:

$$100 \times \frac{T - T_0}{C - T_0} = 50 = PG$$

T is the optical density of the test well after 48 hours drug exposure, $T_0$ is the optical density at time zero, and C is the control optical density, PG is the "percent growth". It is a T/C like parameter that can have values from +100 to −100.

Total Growth Inhibition (TGI) signifies the cytostatic level effect:

$$TGI = 100 \times \frac{T - T_0}{C - T_0} = 0 = PG$$

The $LC_{50}$ is the lethal dose concentration, "net cell killing" or cytotoxicity parameter:

$$LC_{50} = 100 \times \frac{T - T_0}{T_0} = -50 = PG$$

Part A: Comparison of the Dose Response Curves for Compound 1 (chackol) and Paclitaxel.

The $GI_{50}$, TGI and $LC_{50}$ values were calculated by interpolation using the tested concentrations that give PG values above and below the response reference values (e.g. 50 for $GI_{50}$). Dose-response curves are compared for compound 1 and paclitaxel for breast cancer, ovarian cancer, CNS cancer and non-small lung cancer in FIGS. 1–4 respectively. The graphs extend one log unit lower for compound 1 (chackol) showing its greater activity.

Part B: Mean Graphs of TGI (Total Growth Inhibition) for Compound 1 (chackol) and Paclitaxel.

Figures 5, 5A:
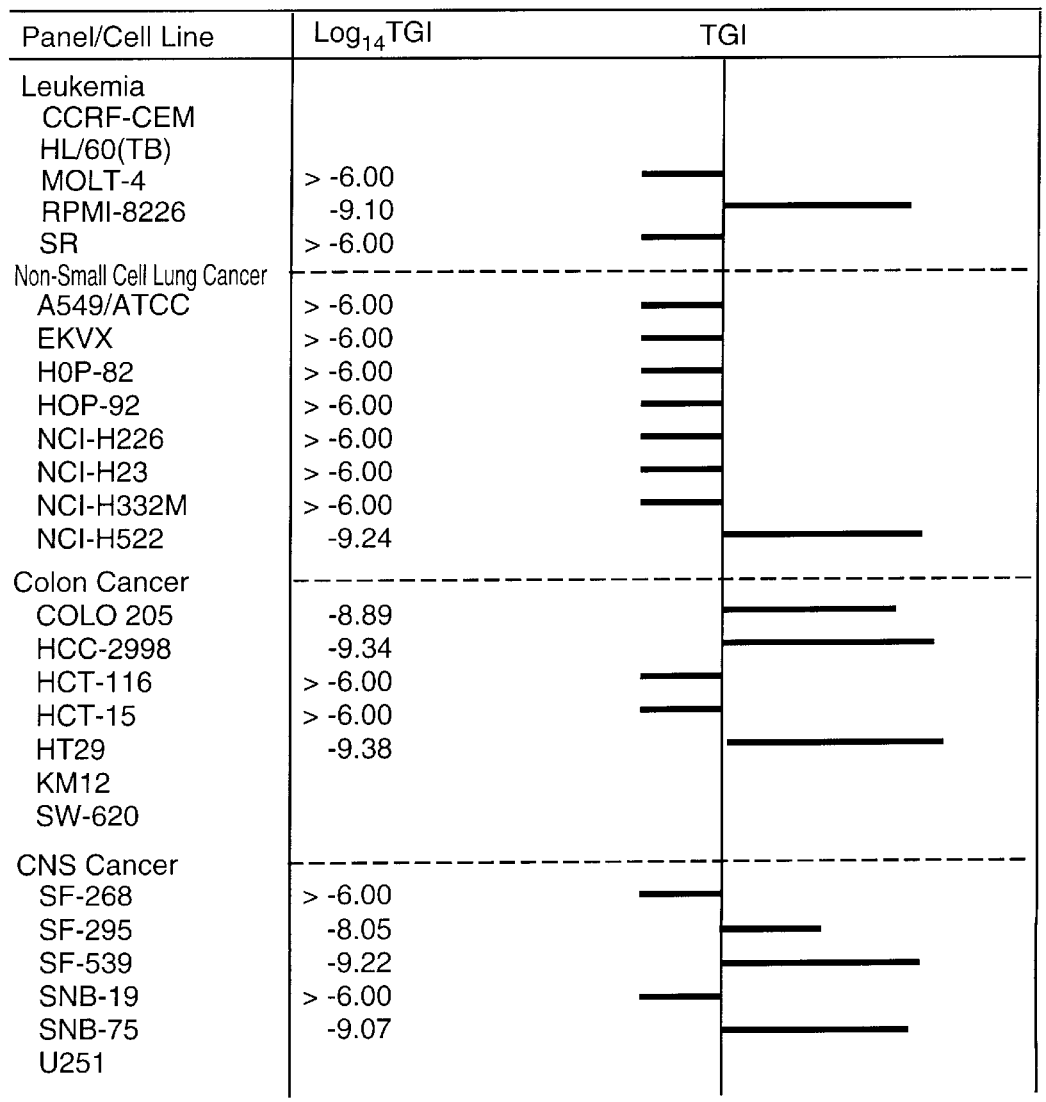
FIG. 5 provides the TGI (Total Growth Inhibition) mean graphs for compound 1 (chackol) and paclitaxel.
Figure 5B:
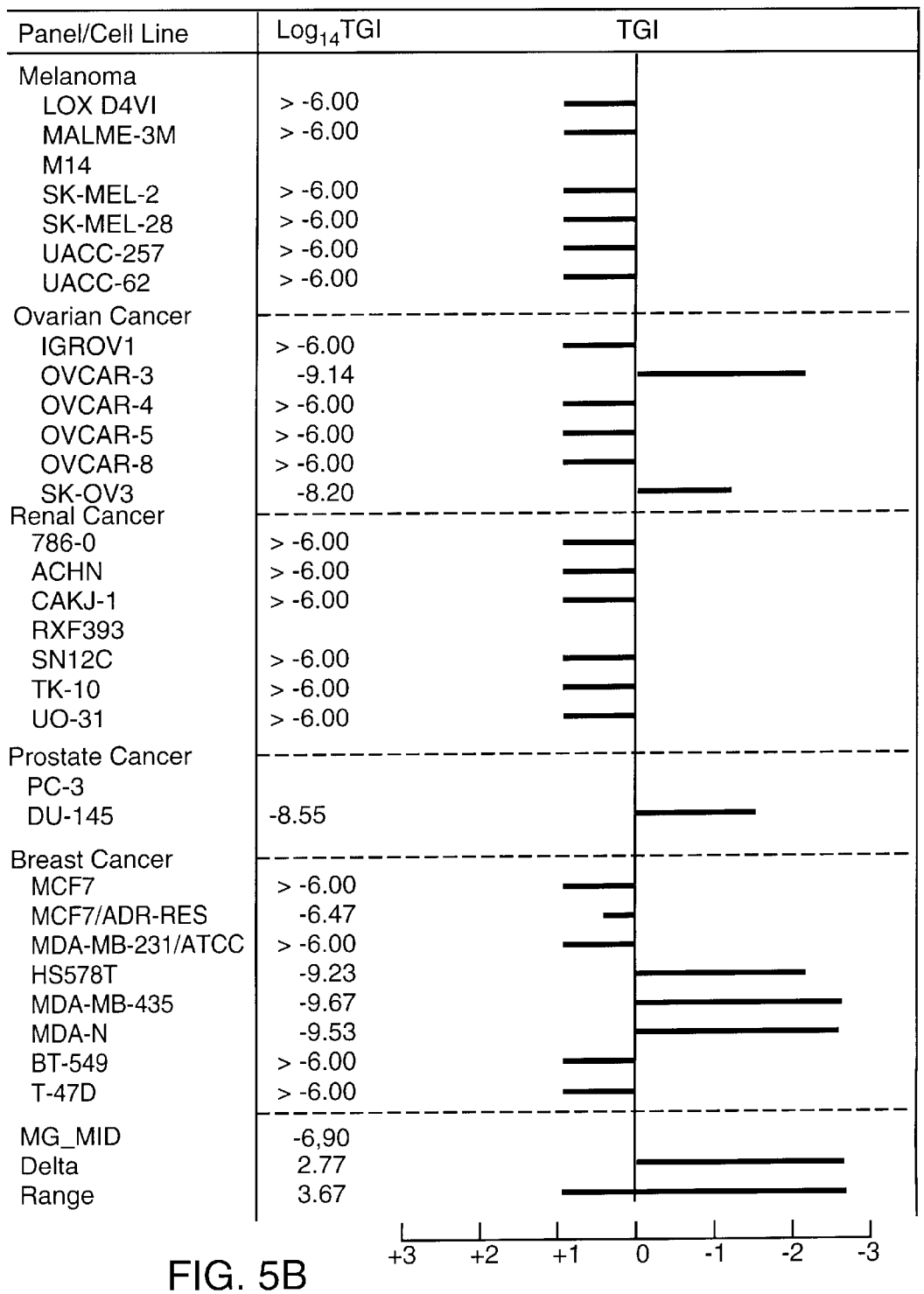
Figure 5C:
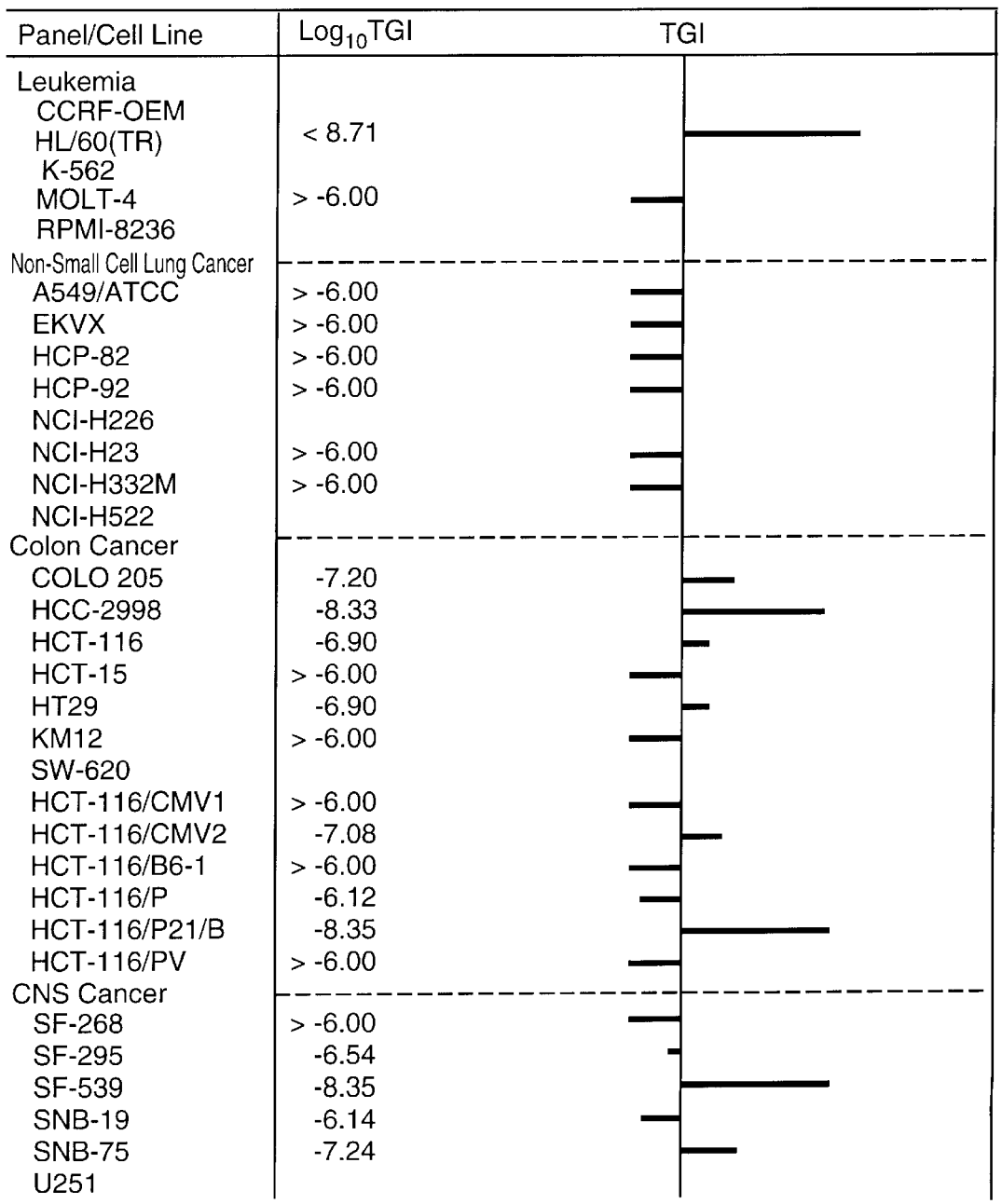
Figure 5D:
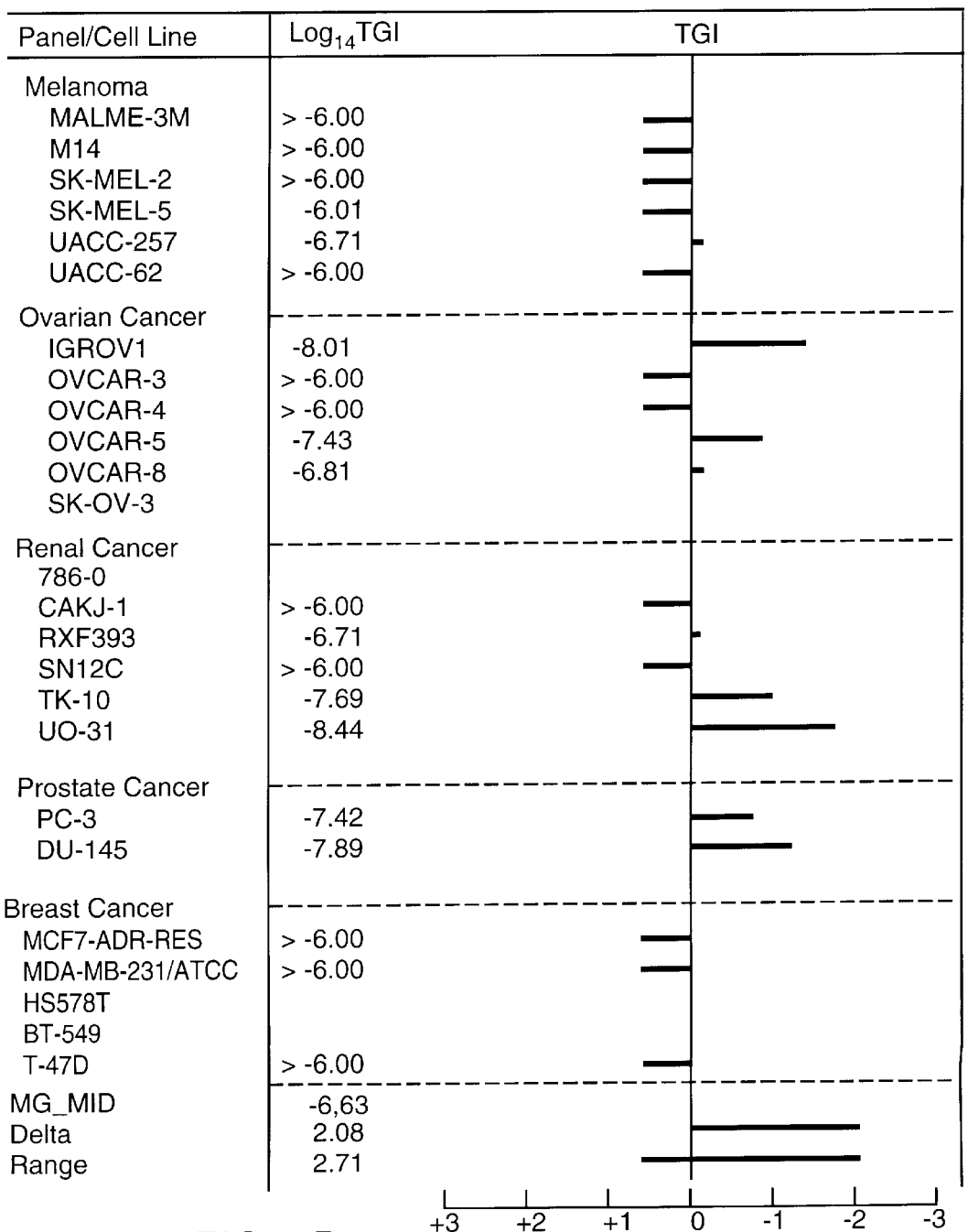

The mean graphs were generated by plotting positive and negative values (deltas), TGI or $LC_{50}$ concentrations, obtained for a given compound. The deltas are plotted horizontally in reference to a vertical line that represents the calculated mean panel for $GI_{50}$, TGI or $LC_{50}$. Bars extending to the right represent sensitivity of the cell line to the test agent in excess of the average sensitivity of all tested cell lines. The positive deltas are plotted to the left of the reference line to represent the less sensitive cell lines to the given agent. Since the bar scale is logarithmic, a bar projecting 3 units to the right of the vertical reference line in a TGI mean graph indicates that the TGI concentration for that cell is 1,000 times less than the panel-average TGI concentration. The mean graphs using TGI for compound 1 (chackol) and paclitaxel are shown in FIG. 5 for comparison.

Compare is a computerized pattern-recognition algorithm and it is a method of determining and expressing the degree of similarity of mean graph profiles, developed by NCI (Boyd and Paull, 1995, Drug Development Research 34: 91–109). A selected particular mean-graph profile or seed is used to probe a given data base, the appropriate delta for each cell line is compared to the corresponding delta value for the same cell line for every mean graph entry in the specified database set. The commercially available SAS statistical program is used to calculate a Pearson product moment correlation coefficient (0.0–1.0) for each set of delta value pairs. Compare correlation coefficients is an excellent tool for structure activity studies. Uniformly high compare correlation coefficients indicated that both compounds 1 (chackol) and 2 (ninnol) shared essentially the same mechanism as that of other tubulin-interactive antimitotics such as paclitaxel, vincristine, and vinblastine. Compare correlation coefficients $GI_{50}$ for compound 1 (chackol), LCONC=-6.00M and paclitaxel LCONC=-4.60M with a Pearson correlation coefficient of 0.789. Similarly for compound 2 (ninnol), LCONC=-6.00M the Pearson correlation coefficient with paclitaxel (LCONC=-4.60M) is 0.747. LCONC is the Lowest CONCentration of drug tested in the dose response curves.

Part C: Growth Inhibition Values ($GI_{50}$) for Compound 1 (chackol) (Table 1) of the Invention as Compared to Paclitaxel.

Comparison of the growth inhibition ($GI_{50}$) values indicate that in general chackol is active at a much lower concentration as compared to paclitaxel. Thus, for ovarian cancer cell lines, OVCAR-3, OVCAR-5 and IGROVI, chackol was 18, 32 and 45 times more active than paclitaxel, respectively. With these cell lines the $GI_{50}$ values for chackol were in the $10^{-10}$ M range (Table 1) while those of paclitaxel were in the $10^{-8}$ to $10^{-9}$ M range. For breast cancer cell lines, MCF-7, ADR-RES and T-47D, chackol was 15, 23 and 14 times more active than paclitaxel, respectively. With these cell lines, the $GI_{50}$ values for chackol were in the range of $10^{-8}$ to $10^{-10}$ M as compared to $10^{-7}$ to $10^{-8}$ M for paclitaxel. For melanoma cell line, UACC-62, chackol is 1490 times more active than paclitaxel. For non-small cell lung cancer line, NCI-H23, chackol is 107 times more active than paclitaxel. For CNS cancer cell line, SF-268, chackol is 28 times more active than paclitaxel ($GI_{50}$ values for chackol and paclitaxel were $2.75 \times 10^{-10}$ M and $7.61 \times 10^{-9}$ M respectively). For CNS cancer SF-295 cell line, chackol is 25 times more active than paclitaxel. For CNS cancer SNB-75 cell line, chackol is 65 times more active than paclitaxel ($GI_{50}$ values for chackol and paclitaxel were $2.1 \times 10^{-10}$ M and $1.36 \times 10^{-8}$ M respectively) (Table 1). For colon cancer cell lines COLO25, HT-29 and HCT-15 chackol was 19, 40 and 7 times more active than paclitaxel, respectively. For leukemia cell lines CCRF-CEM and HL-60 (TB) chackol is 8 times more active than paclitaxel. For renal cancer cell lines RXF-393, SN12C and 786-0 chackol is 23, 16 and 11 times more active than paclitaxel respectively. For prostate cancer cell lines PC-3 and DU-145 chackol is 10 and 12 times more active than paclitaxel, respectively.

TABLE 1

| In Vitro $GI_{50}$ Values for Chackol. | |
|---|---|
| Cell Line | GI50 values (M) |
| Ovarian Cancer | |
| OVCAR-3 | $2.66 \times 10^{-10}$ |
| OVCAR-5 | $1.56 \times 10^{-10}$ |
| OVCAR-8 | $4.37 \times 10^{-10}$ |
| SK-OV-3 | $5.02 \times 10^{-10}$ |
| Breast Cancer | |
| MCF-7 | $2.56 \times 10^{-10}$ |
| MDA-MB-435 | $7.14 \times 10^{-10}$ |
| HS578T | $1.80 \times 10^{-10}$ |
| MDA-MB-435 | $<1.0 \times 10^{-10}$ |
| MDA-N | $1.05 \times 10^{-10}$ |
| T-47D | $8.04 \times 10^{-10}$ |
| Non Small Lung Cancer | |
| A549/ATCC | $5.75 \times 10^{-10}$ |
| EKVX | $1.98 \times 10^{-9}$ |
| HOP-62 | $1.13 \times 10^{-9}$ |
| NCI-H226 | $4.19 \times 10^{-10}$ |
| NCI-H23 | $4.28 \times 10^{-10}$ |
| NCI-H322M | $5.93 \times 10^{-10}$ |
| NCI-H522 | $1.84 \times 10^{-10}$ |
| CNS Cancer | |
| SF-268 | $2.75 \times 10^{-10}$ |
| SF-295 | $1.44 \times 10^{-9}$ |
| SF-539 | $2.20 \times 10^{-10}$ |
| SNB-19 | $3.54 \times 10^{-10}$ |
| SNB-75 | $2.10 \times 10^{-10}$ |
| U251 | $3.63 \times 10^{-10}$ |
| Colon Cancer | |
| COLO205 | $2.47 \times 10^{-10}$ |
| HCC-2998 | $1.52 \times 10^{-10}$ |
| HCT-116 | $2.28 \times 10^{-10}$ |

TABLE 1-continued

In Vitro GI$_{50}$ Values for Chackol.

| Cell Line | GI50 values (M) |
|---|---|
| HCT-15 | 2.79 × 10$^{-8}$ |
| HT-29 | 1.27 × 10$^{-10}$ |
| SW-620 | 3.48 × 10$^{-10}$ |
| Leukemia | |
| CCRF-CEM | 3.13 × 10$^{-10}$ |
| HL-60TB | 2.49 × 10$^{-10}$ |
| MOLT-2 | 4.87 × 10$^{-10}$ |
| RPMI-8226 | 2.66 × 10$^{-10}$ |
| Renal Cancer | |
| 786-0 | 1.33 × 10$^{-9}$ |
| RXF-393 | 4.96 × 10$^{-10}$ |
| SN12C | 4.81 × 10$^{-10}$ |
| Prostate Cancer | |
| PC-3 | 2.76 × 10$^{-10}$ |
| DU-145 | 4.01 × 10$^{-10}$ |

Part D: Total growth inhibition (TGI) of cancer cell lines when treated with chackol as compared to paclitaxel.

Chackol is more active than paclitaxel in total growth inhibition of various cancer cell lines. A few TGI values are compared as examples. Thus, with colon cancer cell line, HT-29, chackol is 303 times more active than paclitaxel. With CNS cancer cell line, SNB-75, chackol is 67 times more active. The TGI values (concentrations) of chackol are very low. on the order of 10$^{-10}$ M compared to paclitaxel on the order of 10$^{-7}$ to 10$^{-8}$ M, indicating the greater sensitivity of chackol towards these cell lines. The TGI values of chackol for breast cancer cell lines, HS578T, MDA-MB-435 and MDA-N, are 5.92×10$^{-10}$ M, 2.15×10$^{-10}$ M and 2.94× 10$^{-10}$ M respectively.

EXAMPLE 5

Water Solubility of Compound 1 (chackol) Compared to Paclitaxel.

The water solubility of compound 1 was determined as an equilibrium concentration at room temperature using HPLC measurements. Compound 1 (chackol) has a water solubility of 240 μg/mL, whereas paclitaxel is extremely insoluble in water, with a reported solubility of 0.25 μg/mL (Vyas, D. M., et al., (1993). Bioorganic and Medicinal Chemistry Letters, 3 (6), 1357–1360).

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A compound of the following formula (Formula I):

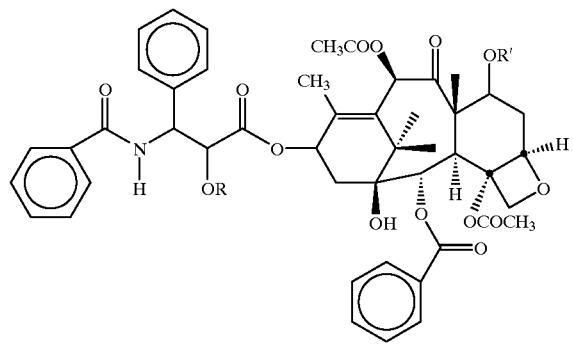

(I)

wherein R and R' are independently selected from the group consisting of a hydrogen atom, X-sugar and XX'-sugar with proviso that at least one of R and R' is X-sugar or XX'-sugar; and wherein X and X' are independently selected from the group consisting of a dicarboxylic acid with from 2 to 12 carbon atoms, an amino dicarboxylic acid with from 1 to 12 carbon atoms and an amino acid.

2. A compound according to claim 1 wherein at least one of R and R' is a group of the formula:

wherein n is an integer of from 1 to 3 and glucose is conjugated as 3-ester.

3. A compound according to claim 1 wherein at least one of R and R' is a group of the formula:

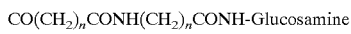

wherein n is an integer of from 1 to 3 and glucosamine is conjugated as an amide.

4. A compound according to claim 1 wherein at least one of R and R' is a group of the formula:

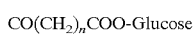

wherein n is an integer from 1 to 3 and glucose is conjugated as an ester.

5. A compound according to claim 1 wherein at least one of R and R' is a group of the formula:

wherein n is an integer from 1 to 3 and glucose-1,2:5,6-diacetonide is conjugated as an ester.

6. A compound according to claim 1 wherein at least one of R and R' is a group of the formula:

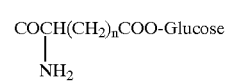

wherein n is an integer from 1 to 3 and glucose as an ester.

7. A compound according to claim 1 wherein at least one of R and R' is a group of the formula:

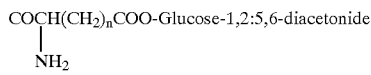

wherein n is an integer from 1 to 3 and glucose-1,2:5,6-diacetonide is conjugated as an ester.

8. A compound according to claim 1 wherein at least one of R and R' is a group of the formula:

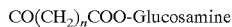

wherein n is an integer from 1 to 3 and glucosamine is conjugated as an ester or as an amide.

9. A compound according to claim 1 wherein at least one of R and R' is a group of the formula:

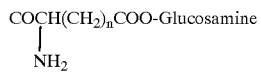

wherein n is an integer from 1 to 3 and glucosamine is conjugated as an ester or as an amide.

10. A compound according to claim 6, which further comprises an acid addition salt selected from the group consisting of HCl and maleate salt.

11. A compound according to claim 7, which further comprises an acid addition salt selected from the group consisting of HCl and maleate salt.

12. A compound according to claim 9, which further comprises an acid addition salt selected from the group consisting of HCl and maleate salt.

13. A paclitaxel derivative selected from the group consisting of:
   2'-(GABA-succinoyl)paclitaxel,
   2'-(glucose-GABA-succinoyl)paclitaxel,
   2'-(glucose-succinoyl)paclitaxel,
   2'-(glucose-glutamyl)paclitaxel,
   2'-(glucosamide-GABA-succinoyl)paclitaxel,
   2'-(glucoseamide-succinoyl)paclitaxel,
   2'-(glucoseamide-glutamyl)paclitaxel,
   7-(GABA-succinoyl)paclitaxel,
   7-(glucose-GABA-succinoyl)paclitaxel,
   7-(glucose-succinoyl)paclitaxel,
   7-(glucose-glutamyl)paclitaxel,
   7-(glucosamide-GABA-succinoyl)paclitaxel,
   7-(glucoseamide-succinoyl)paclitaxel, and
   7-(glucoseamide-glutamyl)paclitaxel.

14. A method for treating tumors which comprises administering to a patient an effective anti-tumor amount of at least one compound according to claim 10.

15. A method for treating tumors which comprises administering to a patient an effective anti-tumor amount of at least one compound according to claim 11.

16. A method for treating tumors which comprises administering to a patient an effective anti-tumor amount of at least one compound according to claim 12.

17. A method for treating tumors which comprises administering to a patient an effective anti-tumor amount of at least one compound according to claim 13.

18. A method for treating a mammal bearing susceptible primary or secondary tumors of the breast, prostate, ovary, central nervous system, brain, lung, skin or colon which comprises administering to said mammal an effective anti-tumor amount of at least one compound according to claim 1.

19. The method of claim 18, wherein said mammal is a human.

20. A method for treating a mammal bearing disseminated tumors which comprises administering to said mammal an effective anti-tumor amount of at least one compound according to claim 1.

21. The method of claim 20 wherein said mammal is a human.

22. A pharmaceutical composition comprising an effective anti-tumor amount of at least one compound according to claim 1 admixed with a pharmaceutically acceptable carrier.

23. A composition of claim 22 selected from a group consisting of injectables, solutions, emulsions, dispersions, food premixes, tablets, pills and capsules.

24. The pharmaceutical composition of claim 22 further comprising of fish oils, components of fish oils, triglycerides, ω-3-fatty acids or ω-3-fatty acid esters.

25. A method for treating tumors which comprises administering to a patient an effective anti-tumor amount of at least one compound according to claim 1.

26. The method of claim 25, wherein the amount of compound administered is in the range of 0.5 mg to 10 mg/kg body weight.

27. A method for treating tumors which comprises administering to a patient an effective anti-tumor amount of at least one compound according to claim 1 in combination with another anti-tumor composition.

28. A method for treating tumors which comprises administering to a patient an effective anti-tumor amount of at least one compound according to claim 1 in combination with cisplatin.

29. A process for producing the compound claimed in claim 1 comprising condensing paclitaxel or a paclitaxel derivative with the sugar moiety.

30. A method for producing a pharmaceutical composition for treating tumors comprising combining paclitaxel and a compound according to claim 1 with a pharmaceutically acceptable carrier.

31. The method of claim 30, wherein the pharmaceutically acceptable carrier is selected from the group consisting of fish oils, components of fish oil, triglycerides, ω-3-fatty acids and ω-3-fatty acid esters.

32. A compound of claim 1, wherein the sugar group is glucose or glucosamine.

33. A compound according to claim 1 wherein at least one of R and R' is a group of the formula:

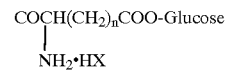

wherein n is an integer from 1 to 3, X is an anion and glucose is conjugated as an ester.

34. A compound according to claim 1 wherein at least one of R and R' is a group of the formula:

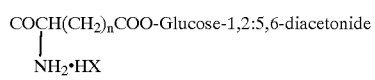

wherein n is an integer from 1 to 3, X is an anion and glucose-1,2:5,6-diacetonide is conjugated as an ester.

35. The method of claim 20, wherein the disseminated tumors are due to leukemia.

36. A pharmaceutical composition comprising an effective anti-tumor amount of a mixture of paclitaxel and at least one compound according to claim 1 admixed with a pharmaceutically acceptable carrier.

* * * * *